United States Patent [19]

Uemura et al.

[11] 4,433,046
[45] Feb. 21, 1984

[54] SILVER HALIDE PHOTOGRAPHIC MATERIAL

[75] Inventors: Morito Uemura; Kenichi Kishi; Satoshi Nakagawa; Shuji Kida, all of Hino, Japan

[73] Assignee: Konishiroku Photo Industry Co., Ltd., Tokyo, Japan

[21] Appl. No.: 383,318

[22] Filed: May 28, 1982

[30] Foreign Application Priority Data

Jun. 3, 1981 [JP] Japan .................................. 56-86066

[51] Int. Cl.³ .......................... G03C 7/16; G03C 7/26
[52] U.S. Cl. .................................... 430/385; 430/553; 430/558
[58] Field of Search ........................ 430/385, 553, 558

[56] References Cited

U.S. PATENT DOCUMENTS

| | | | |
|---|---|---|---|
| 3,476,563 | 11/1969 | Loria | 430/558 |
| 3,839,044 | 10/1974 | Salminen et al. | 430/553 |
| 4,130,427 | 12/1978 | Monbaliu et al. | 430/558 |
| 4,146,396 | 3/1979 | Yokota et al. | 430/558 |
| 4,283,472 | 8/1981 | Gompf et al. | 430/558 |
| 4,310,618 | 1/1982 | Fernandez et al. | 430/553 |

Primary Examiner—J. Travis Brown
Attorney, Agent, or Firm—Jordan B. Bierman; Linda Bierman

[57] ABSTRACT

The invention relates to silver halide photographic materials comprising a support and a light sensitive silver halide emulsion layer containing as a cyan-dye-forming coupler a compound of the formula

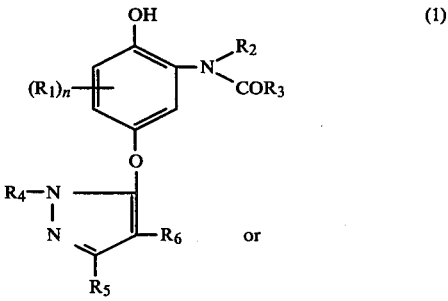

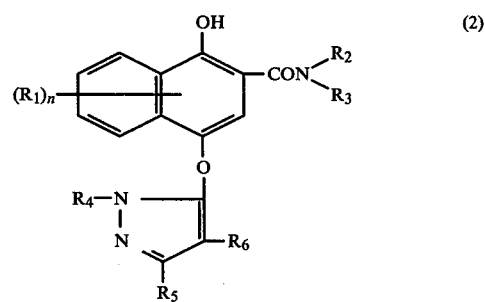

wherein $R_1$ is a halogen atom, an alkyl, alkoxy or acylamino group; $R_2$ and $R_3$ are individually a hydrogen atom, an alkyl or aryl group and $R_2$ and $R_3$ may form a heterocyclic group by the condensation thereof; n is an integer of 0–3; $R_4$ is an alkyl, aryl, acyl or heterocyclic group; $R_5$ is an alkyl, aryl, alkoxy, amino, acylamino, sulfonamide, carboxy, alkoxycarbonyl, carbamoyl, cyano or halogenated alkyl group; and $R_6$ is a hydrogen atom or an alkyl, alkoxy, carboxy, carbamoyl, hydroxy, acyloxy, nitro, amino, azo, acylamino, sulfonamide or acyl group.

6 Claims, No Drawings

SILVER HALIDE PHOTOGRAPHIC MATERIAL

This application claims priority of Japanese Application 86066/1981, filed June 3, 1981.

The present invention relates to a novel photographic coupler, and particularly to a novel cyan coupler for silver halide photographic materials.

Heretofore, a color-image has so far been obtained through such a manner that yellow, magenta and cyan couplers are added into the respective layer and are then coupled respectively to oxide of a phenylene diamine color developing agent.

With the advance of the photographic technique, there has nowadays been a great demand for a higher sensitive and more durable coupler. One of the means to meet the demands has been described in U.S. Pat. No. 3,277,155, that has been given as the so-called "two-equivalent coupler". Thanks to those technique, it has become possible to attain a high sensitivity, and in addition, to save the consumption of silver to be incident thereto, and in its turn, to improve the sharpness (of an image reproduction) to be obtained by thinning the layers. Nevertheless, none of the fully satisfiable "two-equivalent coupler" has been obtained up to this date yet, so that the researches and studies are being continued by the people of every technical standing.

As for the performance required for a photographic coupler, there may be given as the color developability (such as the sensitivity, maximum density, and minimum density) which is one of the photographic characteristics; the durability (such as the raw preservability and image preservability); the absorption waveform; various physical properties required for adding to a silver halide photographic material; and further the easiness in the processes of synthesizing a compound.

It is an object of the invention to provide a silver halide photographic material in which the above conditions are satisfied, and at the same time the color developability, that is one of the photographic characteristics, is improved, and a high sensitivity is rendered.

The objects of the invention can be achieved with a silver halide photographic material comprising a support provided thereon with a light-sensitive silver halide emulsion layer containing as a cyan-dye-forming coupler a compound of the formula

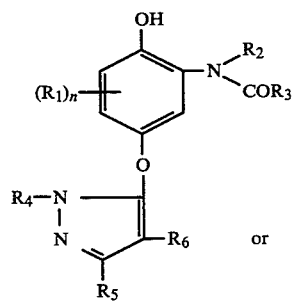 (1)

or

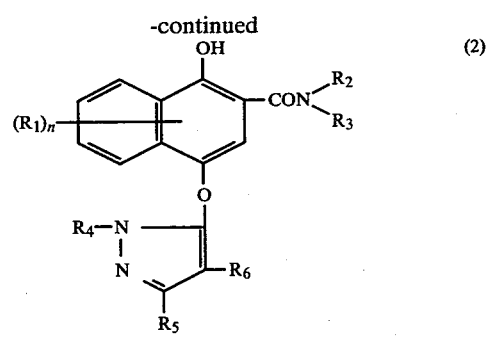 (2)

wherein $R_1$ is a halogen atom, an alkyl, alkoxy or acylamino group; $R_2$ and $R_3$ are respectively a hydrogen atom, an alkyl or aryl group and $R_2$ and $R_3$ may also form a hetero cyclic group by the condensation thereof; n is an integer of 0–3; $R_4$ is an alkyl, aryl, acyl or heterocyclic group; $R_5$ is an alkyl, aryl, alkoxy, amino, acylamino, sulfonamide, carboxy, alkoxycarbonyl, carbamoyl, cyano or halogenated alkyl group, and preferably an alkyl, amino, carboxy or halogenated alkyl; and $R_6$ is a hydrogen atom or an alkyl, alkoxy, carboxy, carbamoyl, hydroxy, acyloxy, nitro, amino, azo, acylamino, sulfonamide or acyl group, and preferably an alkyl, alkoxy, carboxy, carbamoyl, hydroxy, acyloxy, nitro, amino, azo, acylamino, sulfonamide or acyl group.

An alkyl group is hereby designated as an acyl group having one to twenty carbon atoms, among those of which a methyl, ethyl, iso-propyl, n-hexyl, t-decyl, n-octadecyl group and the like are given and there include those substituted by an alkoxy, aryloxy, alkylthio, arylthio, cyano or carboxy group.

An aryl group is hereby designated as a phenyl or naphthyl group which is also allowed to be substituted by an alkyl group, a halogen atom, an alkoxy, hydroxy, carboxy, alkoxycarbonyl, acyl, carbamoyl, cyano, nitro, amino, acylamino, sulfonamide, sulfo, sulfon, sulfamoyl or halogenated alkyl group, with the limitation of using one to five thereof.

A halogen atom is hereby designated as a -Cl, -Br, -I, or -F atom.

An alkoxy group is hereby represented by $-OR_7$, $R_7$ designates an alkyl group.

An acylamino group is represented by

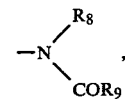

$R_8$ represents hydrogen atom or an alkyl group, and $R_9$ represents an alkyl or aryl group.

A hetero ring is designated as a five or six numbered ring containing one or more oxygen, sulphur, or nitrogen atoms, and they are, for example, a pyrazolyl, pyridyl, imidazolyl, benzimidazolyl, thienyl, triazolyl and benzthiazolyl group.

An acyl group is formularized as

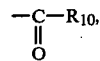

wherein $R_{10}$ represents hydrogen atom or an alkyl, halogenated alkyl or aryl group.

An amino group is formularized as

a sulfonamide group is done as

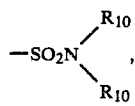

an alkoxycarbonyl group is done as $-COOR_7$, and a carbamoyl group is done as

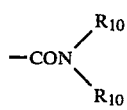

respectively, wherein $R_7$ and $R_{10}$ are same definition as described above.

A halogenated alkyl group is designated as those in which at least one hydrogen atom of an alkyl group is substituted by a halogen atom.

An acyloxy group is formularized as

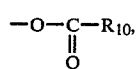

and an azo group is done as $-N=N=R_9$ respectively, wherein $R_9$ and $R_{10}$ are same definition as described above.

In the aforegiven formulae (1) and (2), the desired couplers can be obtained from the compounds of the invention by replacing the substituted groups represented thereby by $R_4$–$R_6$. The inventors have found the fact that the color developability of said couplers have been improved more particularly by introducing a hydrophilic group such as a carboxy, sulfonamide or hydroxy group. In the invention, it is also possible to jointly use two or more compounds of the invention of which the color developability, i.e., the coupling speeds thereof to the oxide of a color developing agent, are different from each other, and further possible to jointly use other cyan couplers too.

The examples of the compounds of the invention are given below, and it is however to be understood that the invention shall not be limited thereto:

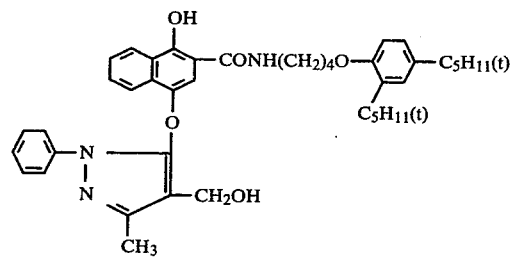

(1)

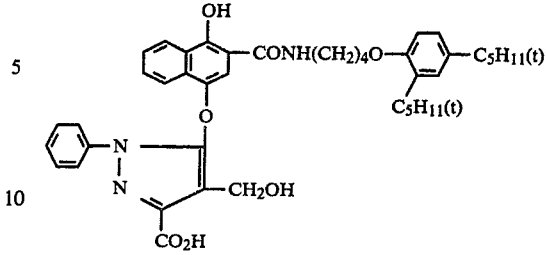

(2)

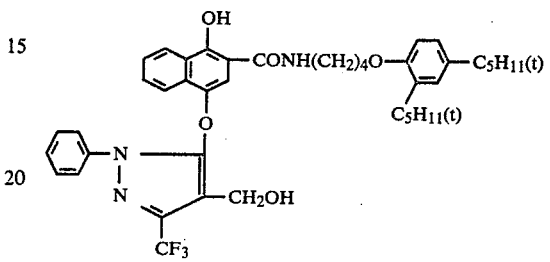

(3)

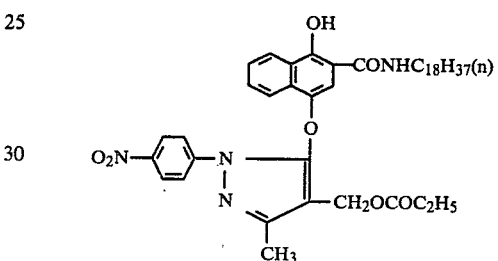

(4)

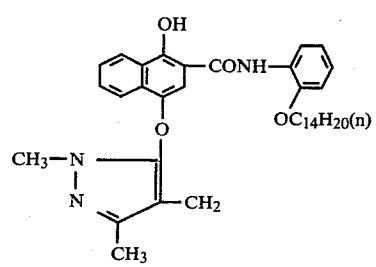

(5)

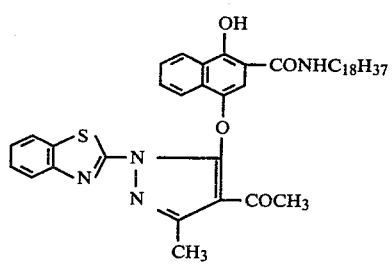

(6)

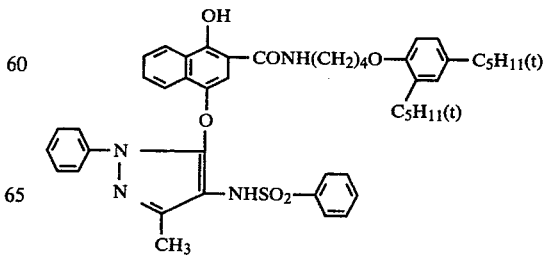

(7)

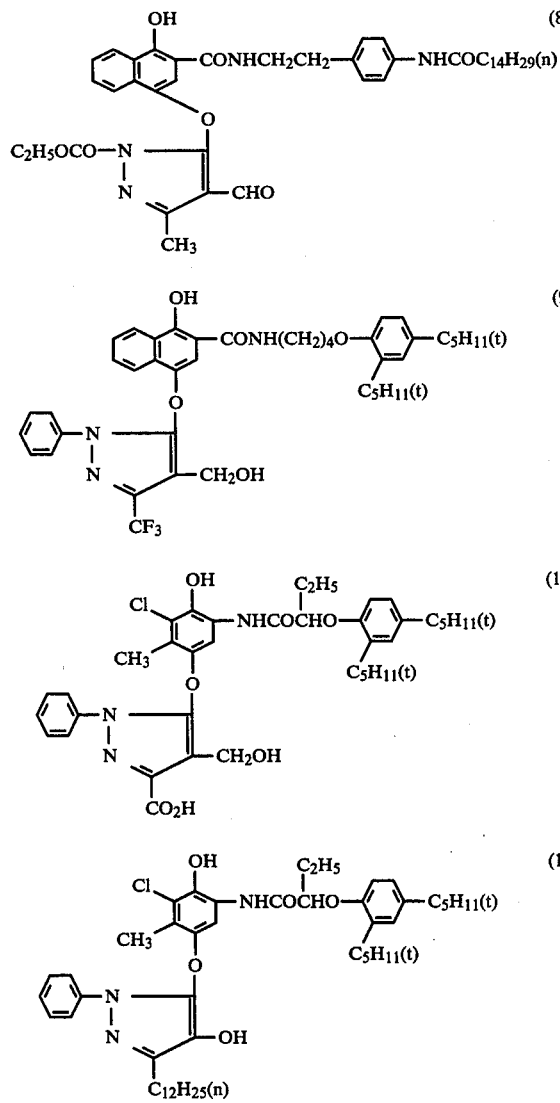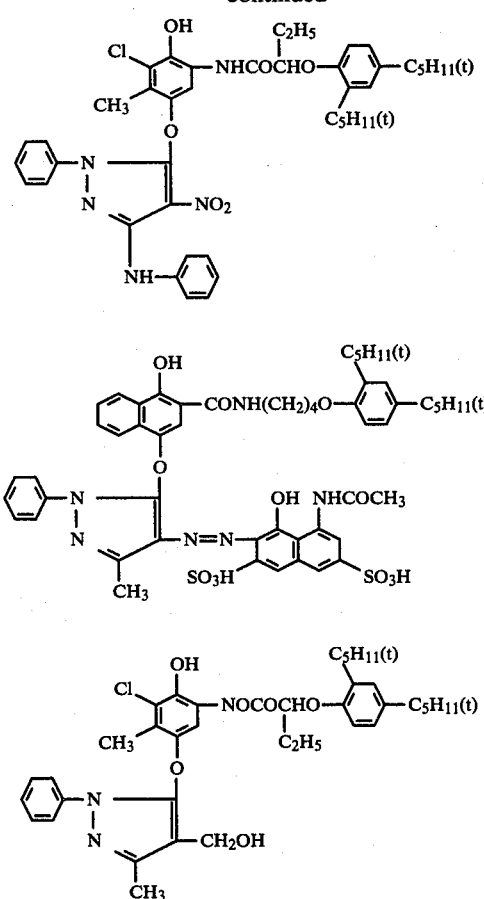
The compounds of the invention can be synthesized through the following synthesizing processes, for example: Synthesis of the compounds formularized in Formula [I]:
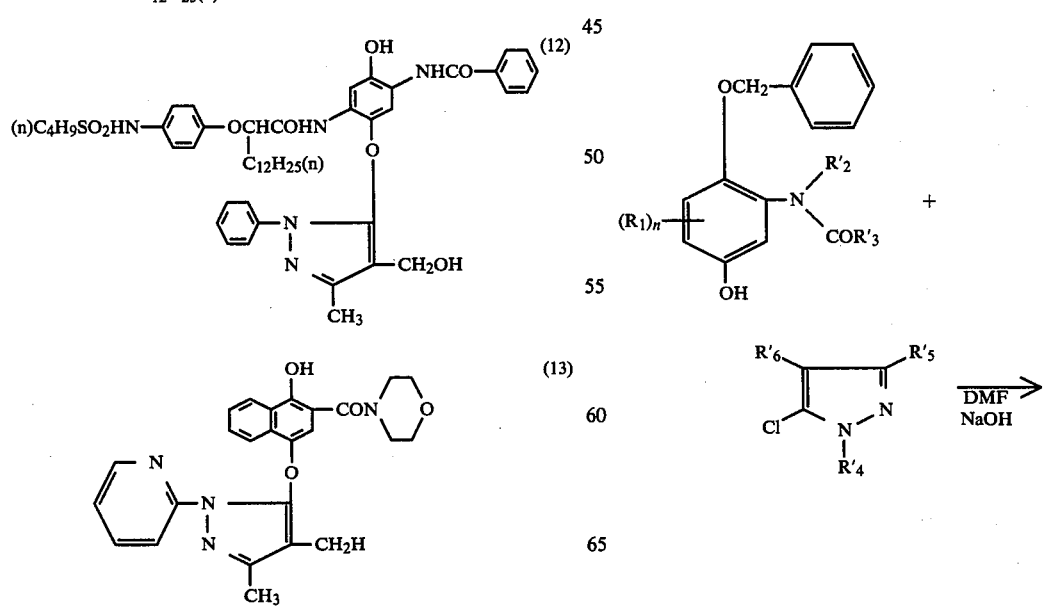

-continued

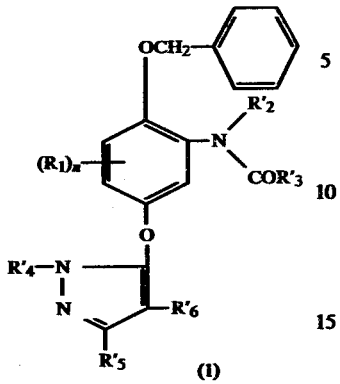

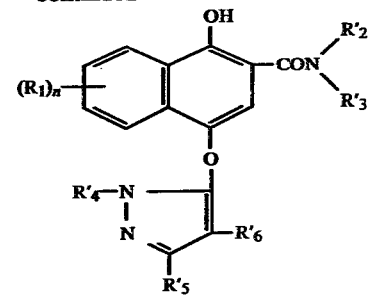

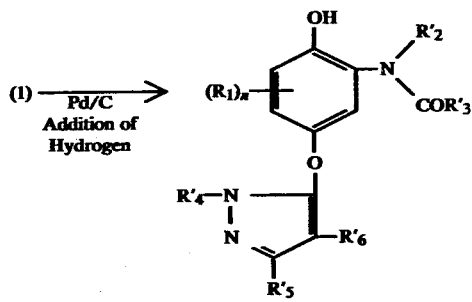

Synthesis of the compounds formularized in Formula [II]:

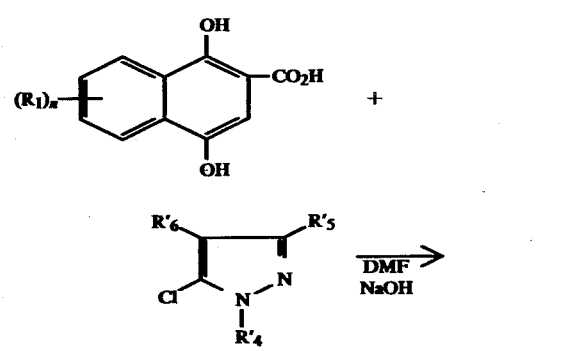

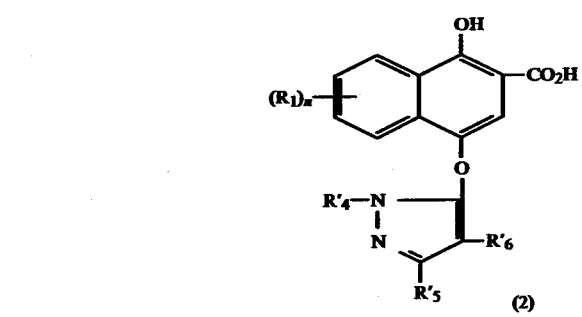

The following is given as the synthesis examples of the compounds described in the examples of the compounds:

The following is the description of the synthesis examples of the compounds of the invention:

(1) Synthesis of Exemplified Compound (1)

The addition of 14 g of 1-phenyl-3-methyl-4-formyl-5-chloropyrazole and 13 g of 1,4-dihydroxy-2-naphthoic acid was made into 80 ml of DMF, and the mixture thus obtained was then added with 10 ml of aqueous solution of 6 g of NaOH slowly and dropwise in an atmosphere of nitrogen. After the internal temperature of the solution thus prepared was kept at 80° C. and for two hours, it was cooled down to 20° C. and 1.2 g of NaBH₄ was then added thereinto to make reaction. One hour later, the reactant solution was poured into a diluted hydrochloric acid to produce crystals, and said crystals were filtrated and washed with methanol, and then were dried up. Thus, there obtained 18 g of 1-hydroxy-4-(1-phenyl-3-methyl-4-hydroxymethyl)pyrazolyl(5)oxy-2-naphthoic acid (the mp: 214° C.). The intermediate thus obtained of 15 g, 7.9 g of DCC (dicyclohexyl carbodiimide), 11.8 g of 2,4-di-t-amyl-phenoxybutylamine and 200 ml of dioxane were agitated at room temperature for eight hours and the urea thus obtained was filtrated, and then the filtrate was vacuum concentrated. The residue thus produced was recrystallized with ethanol-acetone.

Thus, 16 g of exemplified compound (1) were obtained. They were confirmed by NMR mass-spectrum. The mp: 148°–149.5° C.

(2) Synthesis of Exemplified Compound (2)

There obtained in the similar manner as taken in the above item (1).

The agitation of 15 g of 1-hydroxy-4[5-(1-phenyl-3-ethoxycarbonyl-4-hydroxymethyl)pyrazolyloxy]-N-(2,4-di-t-amylphenoxy) butyl-2-naphthamide was made altogether with 100 ml of methanol and 5 ml of aqueous solution containing 2 g of KOH at room temperature for three hours, and the mixture thus obtained was poured into a diluted hydrochloric acid, and extraction was then made with ethyl acetate. The extract thus obtained was dried up with magnesium sulfate and then vacuum concentrated, and a candy-like residue was obtained. Then, the residue was recrystallized with acetonitrile.

Thus, 10 g of Exemplified Compound (2) was obtained. The confirmation thereof was made by NMR mass spectrum. The mp: 98°–105° C.

(3) Synthesis of Exemplified Compound (17)

There were dissolved 11.3 g of 3-[α-(2′,4′-di-(t)amylphenoxy propylcarbonamide]-4-benzyloxy-5-chloro-6-methylphenol and 4.4 g of 1-phenyl-3-methyl-4-formyl-5-chloropyrazole with agitation at room temperature, and then 10 ml of aqueous solution containing 9 g of NaOH were added therein. After the mixture thus obtained was maintained as it was at 80° C. for three hours, it was cooled down to 20° C., added with 0.2 g of powdered $NaBH_4$, and then the agitation was made for one hour. The reactant solution thus prepared was poured into a diluted hydrochloric acid to extract with ethyl acetate, and the extract thus obtained was washed with an aqueous solution of $NaHCO_3$ and an ethyl acetate layer was then vacuum concentrated. Thus, 12.5 g of a yellowish oil-like product were obtained. Said oil-like product of 10 g was dissolved in 100 ml of alcohol and then a hydrogenation was then carried out with palladium carbon as the catalizer at room temperature and atmospheric pressure. After the hydrogen absorption was completed, then the catalizer was filtrated, and the filtrate solution was vacuum concentrated. The residue thus produced was recrystallized with acetonitrile. Thus, 6 g of Exemplified Compound (17) was obtained.

The confirmation thereof was carried out by NMR mass spectrum. The mp: 162°–163° C.

In the case that said coupler according to the invention is to be contained in a silver halide photosensitive material, the amount of said coupler is generally used at the ratio of about 0.07–0.7 mol, and preferably, 0.1–0.4 mol to one mol of silver halide.

Further, when the coupler according to the invention is to be contained in a photosensitive material, a publicly known organic solvent having a high boiling point such as dibutyl phthalate and ethyl acetate may be used to serve as a solvent for such coupler.

The couplers according to the invention can be utilized according to various purposes and can display the excellent characteristics to a variety of the applications.

Silver halide color photographic materials of the invention are used for a silver halide photosensitive material for diffusion transfer system, a negative photosensitive material, a reversal photosensitive material, a positive photosensitive material, a direct positive type photosensitive material and the like.

Silver halide, which is to be used for such various types of silver halide photosensitive materials, is such a silver halide as specified as to silver chloride, silver iodide, silver iodobromide, silver chlorobromide, and silver chloroiodobromide, everyone of which can be prepared in such various processes as a neutral process and an ammonia method in accordance with the kinds of such photosensitive materials. Also, those of a silver halide can be chemically sensitized by making use of an active gelatin, a sulfuric sensitizer (e.g., allylthio carbamide, thio urea or cystine), a selenium sensitizer, a reductional sensitizer (e.g., stannous salt or polyamine), a noble metal sensitizer (e.g., a water-soluble salt of gold, ruthenium, rhodium, indium or the like), independently or in suitable combination thereof.

Further, those of silver halide can be optically sensitized in a desired wavelength region thereof, and to be exemplified, they can be optically sensitized with an optical sensitizer of a cyanine dye such as zeromethin, monomethin, dimethin and trimethin or of a merocyanine dye, which is used independently or jointly therewith.

Still further, as for the supports for said photosensitive materials, there are used the publicly known film or sheet type supports such as paper, laminate paper, glass plate, cellulose acetate, polyester, and polycarbonate.

The photographic materials of the invention each comprises at least a support and a photosensitive layer arranged thereon that may be constituted by various kinds of layers to meet the purposes as described above, and popularly be constituted by more than several layers.

The couplers of the invention may not only be used in suitable combination with each other, but also be used in combination with other two-equivalent and four-equivalent couplers, and further, there are contained in a photosensitive layer having a suitable photosensitive wavelength region with the couplers respectively having various hues of color dyes.

In a silver halide color photographic material according to the invention, a photosensitive layer having some photosensitive wavelength region may be constituted by two or more layers and such photosensitive layers may further be used in combination with each other having different sensitivity, and still further, the couplers to be contained in each of the layers may be those forming a dye in the same color but belonging to a different type from each other, for example, a two-equivalent coupler and a four-equivalent coupler. The embodiments of this kind are carried out with the purpose of further improving a resolving power or a photosensitivity, in general.

Further, the couplers according to the invention may be jointly used with other two-equivalent or four-equivalent couplers, and in the case of using such two-equivalent coupler there can be used the so-called colored coupler (e.g., a coupler that is coupled to a split-off group having an azo group serving as a coupling group at the active site of the coupler) or the so-called DIR coupler (that is a coupler releasing a development inhibitor during a color development process, e.g., a coupler that has a split-off group having a thio group serving as a coupling group at the active site.).

Still further, the photographic material may contain various photographic additives in the photosensitive layers and/or the other constitutional layers thereof (e.g., an interlayer, subbing layer, filter layer, protective layer and image receiving layer), in accordance with the purposes. Such photographic additives include, for example, a stabilizer, a sensitizer, a membrance physical property improver, a hardening agent, a spreading agent, a coupler solvent, the so-called DIR compounds releasing a development inhibitor during a color development process and producing a substantially colorless compound, and besides, an antistatic agent, a deforming agent, an ultraviolet ray absorbent, a fluorescent whitening agent, an antislipping agent, a matting agent, an antihalation agent, an antiirradiation agent or the like; and such a variety of additives may be used independently or jointly with each other.

On the other hand, a color developing solution, that is to color-develop after a photosensitive material is exposed to light, is principally composed of a color developing agent as described above, and the developing agents to be used in the invention are an aromatic primary amine, and inter alia a P-phenylenediamine is of the typical, and to be more concrete they include, for example, diethyl-P-phenyl-enediamine hydrochloride, monomethyl-P-phenylenediamine hydrochloride, dimethyl-P-phenylenediamine hydrochloride, 2-amino-5- diethylamino toluene hydrochloride, 2-amino-5-(N-ethyl-N-dodecylamino)-toluene, N-ethyl-N-β-methanesulfonamide ethyl-3-methyl-4-aminoaniline hydrochloride, N-ethyl-N-β-methanesulfonamide ethyl-4-aminoaniline, 4-N-ethyl-N-β-hydroxyethylaminoaniline and the like.

And, such developing agents may be used independently or jointly with each other two or more thereof, and further used jointly with a black-and-white developing agent such as hydroquinone and the like as required; and still further, said color developing solution contains an alkaline agent such as sodium hydroxide, ammonium hydroxide, sodium carbonate and the like in general and it may be allowed to contain therein a variety of additives, for example, a halogenated alkaline metal such as potassium bromide, or a development adjuster such as citrazinic acid. Such color developing solution is contained in advance in an image recipient material in some type of a diffusion transfer system or the like for example, and in such an art a color developing agent and an alkaline agent are separated from each other and the alkaline agent only is contained or the color developing agent is contained in the process first and then the process is carried out by the solution of the other hand during the development.

Couplers relating to the invention react on the oxidant of a color developing agent produced when a silver halide is developed with such color developing solution as mentioned above to produce a dye or to produce other kind of dye according as the type of dye may be.

In order to remove silver halide or developed silver remaining in a photosensitive material from the system after completed the color development, a bleach-fix solution or the like is used for in general, and inter alia, a silver halide solvent such as sodium thiosulfate or ammonium thiosulfate is used as the component for fixing thereof, while potassium ferricyanide, ammonium iron (II) ethylenediaminetetraacetate, sodium salt iron (II) ethylenediaminetetraacetate or the like is used as the component for bleaching.

The following are the description of the invention to be more concrete, with reference to the examples and it is however understood that the embodiments of the invention shall not be limited to the examples given herein.

EXAMPLE 1

Each of the couplers of the invention (indicated by the number of the aforesaid exemplified examples) of $1.5 \times 10^{-1}$ mol (per mol of silver halide) and each of the control couplers of the same quantity which will be described below were heatedly dissolved respectively in the mixture of dibutylphthalate of which the weight by gram is correspondingly same as that of each of the said two kinds of couplers and ethylacetate of the quantity doubled the above quantity, and there were then added with 1000 ml of 5% gelatin solution containing 120 ml of 5% sodium dodecyl-benzene sulfonate, and the emulsifiable dispersion was carried out by means of a colloid mill.

The dispersion solution thus obtained was added in 1000 ml of silver iodobromide gelatin emulsion (the proportion thereof was silver iodide 6 mol%: silver bromide 94 mol%), and the mixture thus obtained was coated over to a film base and dried up, and thus the samples of silver halide color photographic material were prepared. The thickness and the amount of silver coated were $6\mu$ and 3.5 $g/m^2$, respectively.

Those samples were exposed to light through a wedge in an ordinary process and the following process were applied thereto.

| Process | Time processed | |
|---|---|---|
| | min. | sec. |
| Color developing | 3 | 15 |
| Bleaching | 6 | 30 |
| Washing | 3 | 15 |
| Fixing | 6 | 30 |
| Washing | 3 | 15 |
| Stabilizing bath | 1 | 30 |

The following was the composition of the processing solution used in each step of the process:

[Composition of the Color Developing Solution]

| 4-amino-3-methyl-N—ethyl-N—(β-hydroxyethyl)-aniline sulfate | 4.75 g |
|---|---|
| Sodium sulfite, anhydrous | 4.25 g |
| Hydroxyamine ½ sulfate | 2.0 g |
| Potassium carbonate, anhydrous | 37.5 g |
| Sodium bromide | 1.3 g |
| Nitrilotriacetic acid. 3 sodium salt (monohydrate) | 2.5 g |
| Potassium hydrochloride | 1.0 g |
| Add water to make | 1 ltr. |
| Adjust with the use of potassium hydrochloride the pH value to | 10.0 |

[Composition of the Bleaching Solution]

| Ethylenediaminetetraacetic acid iron ammonium salt | 162.0 g |
|---|---|
| Ethylenediaminetetraacetic acid 2 ammonium salt | 10.0 g |
| Ammonium bromide | 150.0 g |
| Glacial acetic acid | 10.0 ml |
| Add water to make | 1 ltr. |
| Adjust with the use of ammonia water the pH value to | 6.0 |

[Composition of the Fixing Solution]

| Ammonium thiosulfate (50% solution) | 100.0 ml |
|---|---|
| Sodium sulfite, anhydrous | 12.4 g |
| Add water to make | 1 ltr. |
| Adjust with the use of acetic acid the pH value to | 6.5 |

[Composition of the Stabilizing Solution]

| Formalin (37% solution) | 5.0 ml |
|---|---|
| Konidux (mfd. by Konishiroku Photo Ind. Co., Ltd.) | 7.5 ml |
| Add water to make | 1 ltr. |

The developments were carried out under the conditions mentioned above.

Density of each image thus obtained was measured by means of Densitometer Model PD-7R (mfd. by Konishiroku Photo Ind. Co., Ltd.) and the results therefrom are shown in Table 1.

In order to inspect the light-resistance and humidity resistance of each image thus obtained, the each one was exposed to xenon light by means of a xenon fademeter for twenty hours and was then put into a thermostat and humidistat chamber whose relative humidity was at 80% at 60° C. The tests were carried out after two weeks for the initial density of 1.0 and then the stability of each coupler was measured by making use of the dye remaining rate based on the density obtained by said tests.

TABLE 1

| Sample No. | Coupler | Sensitivity | Fog | Max. Density | Light Resistance (%) | Humidity Resistance (%) |
|---|---|---|---|---|---|---|
| 1 | Control coupler A | 100 | 0.14 | 1.31 | 91 | 84 |
| 2 | Control coupler B | 115 | 0.16 | 1.55 | 90 | 88 |
| 3 | Control coupler C | 131 | 0.17 | 1.98 | 88 | 82 |
| 4 | Exemplified compound 1 | 128 | 0.15 | 2.05 | 93 | 85 |
| 5 | Exemplified compound 2 | 169 | 0.21 | 2.54 | 90 | 86 |
| 6 | Exemplified compound 4 | 142 | 0.18 | 2.33 | 91 | 84 |
| 7 | Exemplified compound 10 | 130 | 0.14 | 2.11 | 93 | 87 |

Control Coupler A

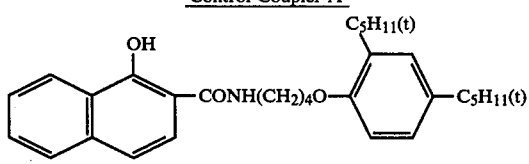

Control Coupler B

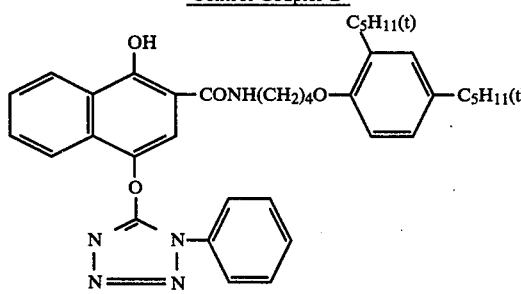

(Compound described in Japanese Patent Publication Open to Public Inspection No. 37425/1972)

Control Coupler C

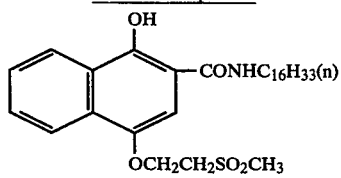

As is seen from Table 1, the images having excellent color developability and high sensitivity were obtained from the compounds of the invention.

EXAMPLE 2

Emulsion used in Example 1 was coated over to a sheet of polyethylene coated paper and dried up. The couplers used in this example were shown in Table 2 and the amounts added thereof were $2.0 \times 10^{-1}$ mol (per mol of silver halide), respectively.

The samples thus obtained were processed in the similar steps to those taken in Example 1, and the results therefrom are shown in Table 2.

Control Coupler D

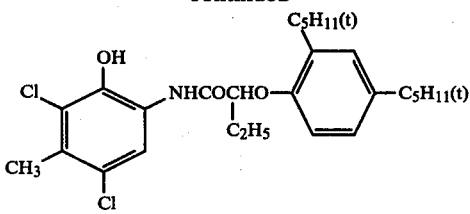

Control Coupler E

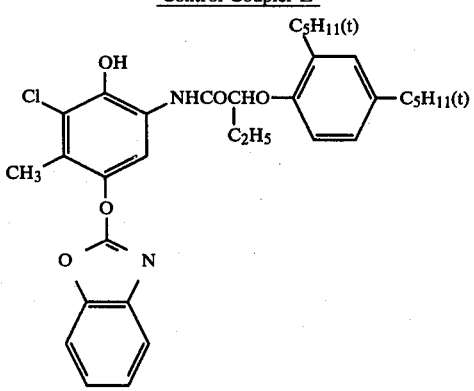

TABLE 2

| Sample No. | Coupler | Sensitivity | Fog | Max. Density | Light Resistance (%) | Humidity Resistance (%) |
|---|---|---|---|---|---|---|
| 8 | Control coupler D | 100 | 0.13 | 1.84 | 94 | 82 |
| 9 | Control coupler E | 112 | 0.15 | 2.05 | 95 | 85 |
| 10 | Exemplified compound 11 | 148 | 0.18 | 2.88 | 98 | 93 |
| 11 | Exemplified compound 12 | 125 | 0.09 | 2.45 | 97 | 95 |
| 12 | Exemplified compound 17 | 128 | 0.12 | 2.60 | 99 | 88 |

As is seen from Table 2, the compounds of the invention are excellent in the color developability and satisfactory in the image durability in comparison with the conventional couplers.

What is claimed is:

1. A silver halide photographic material comprising a support provided thereon with a light-sensitive silver halide emulsion layer containing as a cyan-dye-forming coupler a compound of the formula

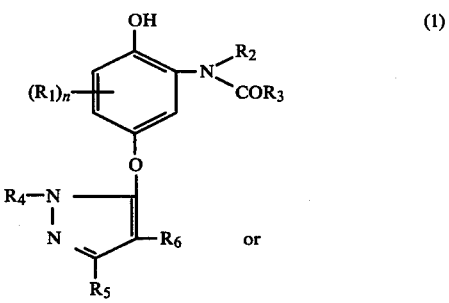

(1)

-continued

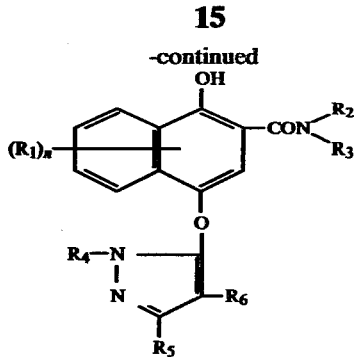

(2)

wherein $R_1$ is a halogen atom, an alkyl, alkoxy or acylamino group; $R_2$ and $R_3$ are respectively a hydrogen atom, an alkyl or aryl group and $R_2$ and $R_3$ may form a heterocyclic group by the condensation thereof; n is an integer of 0–3; $R_4$ is an alkyl, aryl, acyl or heterocyclic group; $R_5$ is an alkyl, aryl, alkoxy, amino, acylamino, sulfonamide, carboxy, alkoxycarbonyl, carbamoyl, cyano or halogenated alkyl group; and $R_6$ is a hydrogen atom or an alkyl, alkoxy, carboxy, carbamoyl, hydroxy, acyloxy, nitro, amino, azo, acylamino, sulfonamide or acyl group.

2. A silver halide photographic material according to claim 1, wherein $R_5$ is an alkyl, amino, carboxy or halogenated alkyl group.

3. A silver halide photographic material according to claim 1, wherein $R_6$ is an alkyl, alkoxy, carboxy, carbamoyl, hydroxy, acyloxy, nitro, amino, azo, acylamino, sulfonamide or acyl group.

4. A method for producing a cyan dye image by color development of an exposed silver halide photographic material of claim 1.

5. A method for producing a cyan dye image by color development of an exposed silver halide photographic material of claim 2.

6. A method for producing a cyan dye image by color development of an exposed silver halide photographic material of claim 3.

* * * * *